United States Patent [19]

Visscher

[11] 4,434,180
[45] Feb. 28, 1984

[54] INSECT CONTROL METHODS WITH ABSCISIC ACID

[76] Inventor: Saralee N. Visscher, 516 S. 6th Ave., Bozeman, Mont. 59715

[21] Appl. No.: 364,647

[22] Filed: Apr. 2, 1982

Related U.S. Application Data

[63] Continuation of Ser. No. 133,631, Mar. 27, 1980, filed as PCT US79/00546 Jul. 27, 1979, published as WO80/00295 Mar. 6, 1980, § 102(e) date Mar. 27, 1980, abandoned, which is a continuation-in-part of Ser. No. 929,116, Jul. 28, 1978, Pat. No. 4,209,530.

[51] Int. Cl.$^3$ .............................................. A01N 37/00
[52] U.S. Cl. ............................ 424/317; 424/DIG. 12
[58] Field of Search ........ 424/317, 331, 343, DIG. 12

[56] References Cited

U.S. PATENT DOCUMENTS 3,958,025  5/1976  Livingston ........................ 424/317
4,209,530  6/1980  Visscher ............................ 424/317

OTHER PUBLICATIONS

Eidt et al., J. of E con. Ent. 63: 1966–1968 (1970).
Sláma, Annual Review of Biochemistry, vol. 40, pp. 1096–1097 (1971).
Scheurer, Symp. Biol. Hung., 16, pp. 255–259 (1976).
Milborrow, Ann. Rev. Plant Physiol., 25, 259–307 (1974).
Eidt et al., The Canadian Entomologist, 100: 1278–1279 (1968).

Primary Examiner—Leonard Schenkman
Attorney, Agent, or Firm—Lowe, King, Price & Becker

[57] ABSTRACT

There are disclosed insect control compositions comprising abscisic acid and its analogs, and a method of controlling insects by inhibiting the reproduction thereof which comprises applying abscisic acid or an analog to food on which the insects will feed or directly to insect eggs.

2 Claims, No Drawings

INSECT CONTROL METHODS WITH ABSCISIC ACID

This is a continuation, of application Ser. No. 133,631, filed Mar. 27, 1980, filed as PCT US79/00546, Jul. 27, 1979, published as WO 80/00295 Mar. 6, 1980, § 102(e), date Mar. 27, 1980 now abandoned, which is a continuation-in-part of Ser. No. 929,116, Jul. 28, 1978, Pat. No. 4,209,530; which is the National Phase filing of International Application No. PCT/US79/00546, filed July 27, 1979; for which an application was originally filed in the United States on July 28, 1978 and designated Serial No. 929,116, now U.S. Pat. No. 4,209,530, issued June 24, 1980.

FIELD OF THE INVENTION

This invention relates to novel insect control compositions and to novel methods for the control of insects. More particularly, the invention relates to a composition comprising abscisic acid and/or its analogs, and to a method of controlling insects by inhibiting the reproductive ability of the insects.

BACKGROUND ART

Abscisic acid is a naturally occurring plant hormone which has been found to be useful in the treatment of a vitamin deficiency in man, animal and the avian species. See U.S. Pat. No. 3,958,025 to Livingston. This hormone has been used to delay budbreak of certain plants and thereby to exert an insect control effect. This approach is based upon reducing the food supply available to phytophagous insects. See D. C. Eidt and C. H. A. Little, *The Canadian Entomologist*, 100, 1278–1279 (1968). This hormone has also been tested for its effect, when ingested, on spruce budworm. See D. C. Eidt and C. H. A. Little, *Journal of Economic Entomology*, 63, 1966–1968 (1970). Eidt and Little conclude that the development of the budworm is not affected and state that their data is inconclusive as to affects on pupal size, development time, fecundity, and egg viability since the number of budworms tested was too small. S. Scheurer, in *The Host-Plant in Relation to Insect Behavior and Reproduction*, T. Jeremy, Ed., Plenum Press, New York, pp. 255–259 (1976), reports that when plants of Vicia sp. are treated with abscisic acid and fed to aphids, there is observed an increased size of the $V_1$ offspring, a decrease in maturation time, and an increase in reproduction of the $V_1$ offspring. The chemistry and physiology of abscisic acid and its analogs are described by Milborrow, Ann. Rev. Plant Physiol. 1974, 25. 259–307.

In addition to the above art, there have also been approaches to insect control which require chemical substances such as the chlorinated hydrocarbons. These approaches, however, have the disadvantage of employing substances which are not limited in toxicity to insects.

DISCLOSURE OF INVENTION

It is accordingly one object of the present invention to provide a composition for insect control.

A further object of the present invention is to provide a composition for insect control which is not limited only to its effect on those insects directly affected, but will often result in decreased insect population by death when ingested at high doses by the insect, or when ingested in smaller doses, will result in sterility or a reduction in the ability to reproduce.

A still further object of the present invention is to provide a method for insect control which has the capability of inhibiting the ability of reproduce of the insects.

Other objects and advantages of the present invention will become apparent as the description thereof proceeds.

In satisfaction of the foregoing objects and advantages, there are provided by this invention compositions for controlling insects comprising a reproduction inhibiting amount of abscisic acid or its analogs. There are further provided methods for controlling insects by affecting the reproduction thereof, said method comprising the application to foods on which the insects feed of a reproduction-inhibiting amount of abscisic acid or ovicidal treatment directly.

DETAILED DESCRIPTION OF THE INVENTION

As indicated above, the present invention is concerned with a novel insect control composition and with a novel method for controlling insects by inhibiting the reproduction thereof. The present invention is based upon the surprising discovery that abscisic acid and/or its analogs, when ingested, inhibits the reproduction of insects in low dosage amounts, and may be lethal in high dosage amounts. In addition, abscisic acid has a direct ovicidal effect. According to the present invention, there are provided insect control compositions containing abscisic acid, its analogs, and/or derivatives. Also provided are insect control methods comprising applying abscisic acid to foods on which insects will feed or applying the abscisic acid so as to obtain a direct ovicidal effect.

Abscisic acid is a naturally occurring plant hormone which is found in certain parts of many varieties of plants. Abscisin II and dormin are names previously used for this plant hormone. The structural formula of the hormone is set forth below.

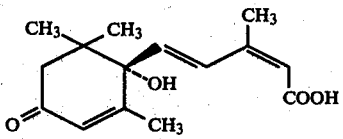

Abscisic acid, sometimes referred to herein as ABA, is known to cause leaf abscission. It is also known to produce a state of dormancy in roots and leaves and to cause ripening of fruits. The action of abscisic acid in producing dormancy opposes the growth promoting action of gibberellic acid, another naturally occurring plant hormone. The hormone has been isolated from those plants in which it naturally occurs and has also been synthesized. For use in the present invention, either the naturally occurring or synthetic forms or analogs which have the same biological activity as a result of their similar molecular structure, such as phaseic acid, dihydrophaseic acid, abscisic alcohol, or aldehyde or xanthoxin compounds, are suitable. All of these materials have the basic nucleus of absicisic acid. Mixtures may also be used. Stereoisomers and mixtures thereof are included within the term abscisic acid.

In the present invention, the abscisic acid can be applied in any manner but is preferably applied in suitable carriers and/or additives. Suitable carriers and additives may be solid or liquid, and correspond to the substances common in formulation practice, such as solvents, dispersing agents, wetting agents, adhesives, thickeners and binders. Other additives may be employed to reduce spray drift and aerosol formation and regulate viscosity, according to known practices.

Formulations which can be prepared include solid preparations such as dusts, scattering agents and granulates of several types. Liquid preparations can also be formulated. Examples of liquid preparations are solutions and water dispersible concentrates such as wettable powders, pastes and emulsions. These formulations are made in a manner commonly known in practice and in this regard the disclosures of U.S. Pat. Nos. 3,973,028 and 3,975,522 are hereby incorporated by reference. Generally, these formulations are produced in a manner known per se by the intimate mixing and/or grinding of the hormone with a suitable carrier, optionally with the addition of dispersing agents or solvents which are inert to the hormone.

Conveniently, the abscisic acid-containing compositions are stored and shipped in the form of water-dispersible solutions or wettable powders and are diluted with water just prior to spraying. In order to obtain a uniform application of the hormone, it is best to apply it to plants using a carrier or diluent. Water and/or ethyl alcohol are very suitable carriers or diluents, but the addition of compounds to render the abscisic acid impermeable to the plant may be necessary in some instances to avoid altering plant growth.

A suitable means of applying the composition of the present invention to insect food such as a host plant is by spraying. One type of spraying system which is well known in the art is foliar spraying, as illustrated by U.S. Pat. No. 3,973,028. However, there may be used any other means of application by which the composition is made available for ingestion by the insect.

The preferred amount of abscisic acid required in the insect control composition is an amount which inhibits the reproduction of the insect being treated and which is nonlethal to the insect or lethal when ingested in large amounts. From the illustrative embodiment set forth below, a standard is provided by which a worker skilled in the art can select the concentration which will meet his needs.

From these statements, it will be understood that the abscisic acid material can be applied to plants or other foods which are fed on by insects to inhibit the reproducing capability of the insect. In this aspect, the abscisic acid material is applied in sufficient amounts so as to obtain a concentration of from about 6 mg per liter to 600 mg per liter, preferably about 6 mg/l to 60 mg/l on the food on which the insect feeds. Concentrations greater than these values, for example, about 600 mg per liter and higher, are also effective in being lethal to the insects.

An exemplary insect control composition of the present invention is made by dissolving the selected amount of abscisic acid or equivalent in a small amount of 95% ethanol and then diluting the resulting solution in a large amount of water as the carrier.

It is contemplated that the abscisic acid-containing composition of the present invention is useful for the control of all plant-eating insects and is particularly effective for controlling the grasshopper families of insects, i.e., the Tettigoniidae and Locustidae. Insects included within these general classes are: grasshoppers, katydids, cicadae, locusts and Mormon crickets. Species of grasshoppers within these general groups on which the abscisic acid has been shown to be effective are *Aulocara elliotti* (Thomas), *Xanthippes corallipes,* and *Melanoplus sanguinipes.*

The invention has also been found to be operable on other insects. For example, it has been found that a reproduction-inhibiting effect is achieved on the *Oncopeltus fasciatus,* the milkweed bug (Order Hemiptera, Insecta) and the aphid *Rhopalosiphum padi.* Effectiveness on these insects shows that the invention is also applicable to plant-eating insects in general (milkweed bug) and viviparous insects (aphids), in these dosage amounts. According to the invention, control of these insects is obtained by applying the plants on which these insects feed an amount of abscisic acid which reduces or inhibits the ability of the insects to reproduce. The amount of abscisic acid required to achieve the reproduction inhibiting effect is about 6 mg/l to 60 mg/l applied to the plant or other food on which the insects feed.

It has also been found that the abscisic acid is effective in reducing the ability of non-leaf eating insects to reproduce using the same dosage amounts. Thus, it has been found that the ability to reproduce of insects such as houseflies and fruit flies can be affected by use of abscisic acid. In the case of the housefly, *Musca domestica,* it was found that application of abscisic acid to food fed to the ordinary housefly resulted in a clear reduction in the ability of the housefly to reproduce.

It has further been found that abscisic acid also affected the ability of the fruit fly, *Drosophila melanogaster,* to hatch when the abscisic acid was used for direct ovicidal affect. In this procedure, the abscisic acid was used to directly treat eggs of the fruit fly.

Both of these experiments show a clear reduction in the ability of the flies to reproduce, either when applied directly to the eggs, or fed to the insects in their food in the same dosage amounts as for the leaf-eating insects. On a large scale, the treatment of flies with the abscisic acid could be carried out by direct spraying of the eggs of the insects, or by the use of traps. Since abscisic acid is a naturally occurring plant hormone, it could also be fed to animals such as cattle for ingestion and would then be present in the resulting manure in which the flies would lay their eggs so that direct treatment could be obtained.

It will therefore be understood that the present invention provides methods and compositions for the control of a wide variety of insects, both of the leaf-eating type and other types. This control is achieved by causing the insect to feed on plants or other food which have been treated with the indicated amount of abscisic acid. As a result, the reproductibility of the insects is reduced by action on fecundity and egg viability of the insect. Similarly, it has been found that insects such as houseflies and fruit flies which are not necessarily leaf-eating, can be controlled by reducing their ability to reproduce by treatment of their food with abscisic acid or direct application of abscisic acid to eggs of these insects.

BEST MODE OF CARRYING OUT THE INVENTION

The following examples of the present invention are presented to illustrate the insect control effect of abscisic acid using a variety of insects. However, it will be appreciated by one skilled in the art that these embodiments are merely illustrative and that there are numerous modifications including those disclosed above which are within the scope of the present invention.

EXAMPLE I

The grasshopper, *Aulocara elliotti* (Thomas), was collected as nymphs and as young adults at a wild population site near Simms, Mont., transported to Bozeman, Mont., and divided into groups with three pairs of nymphs maintained per cage until they became adults. The adults are separated one pair to a cage and are maintained under hot temperatures which fluctuate diurnally from 24°–29.5° C.

The growing host plant, western wheatgrass, was transplanted from a field site at the Agricultural Experiment Station Farm near Red Bluff, Mont., onto tables in a greenhouse where it was maintained under hot temperatures which alternate diurnally from approximately 24°–29.5° C.

Twice each week, on Tuesdays and Fridays, grasshopper pairs were fed the greenhouse grass which was freshly cut on the morning of the feeding day and then treated with an abscisic acid-containing composition prepared according to the present invention. The feedings were continued until all grasshoppers were dead. The number of eggs laid and the number of viable eggs were recorded throughout the lifetime of each female grasshopper.

The abscisic acid-containing composition was prepared by dissolving synthetic crystalline abscisic acid (mixed isomers, No. A-7383, Sigma Chemical Company) in 20 ml of 95% ethanol and then diluting the resulting solution to a volume of one liter with distilled water.

The freshly cut greenhouse grass was treated with the composition containing abscisic acid by applying the composition thereto. This was achieved by dipping the grass leaves in the solution and then letting the cut ends stand in the same solution for about 4 hours. Individual feeding vials were assembled by wrapping cut grass with a urethane foam strip about one inch in diameter and then by fitting the bundle of cut grass into a plastic pill vial. The cut grass was then watered with the solution and as this solution evaporated or was taken up by the grass, the vial was rewatered with distilled water.

In this illustrative embodiment, two insect control compositions were formulated which contain 6 mg and 60 mg of abscisic acid per liter. The result of using these compositions is set forth in the following Table. In addition to using compositions containing these two concentrations of abscisic acid, a composition was prepared containing 600 mg of abscisic acid per liter. This higher concentration composition was determined to be lethal to the insect.

The insect control effect of the abscisic acid-containing composition of the present invention was demonstrated by comparison of the above results with a Control, wherein all particulars of the above illustrative embodiment were followed except that the greenhouse grass was not treated with an abscisic acid-containing composition. The result of this Control is set forth in the Table.

By the data set forth in Table I for the abscisic acid-containing compositions and for the Control, the reproduction inhibiting action of abscisic acid is demonstrated. Accordingly, use of an insect control composition containing abscisic acid ranging in concentration from at least about 6 mg per liter to about 60 mg per liter is very suitable in the practice of the present invention, with concentrations in the lower part of the range being preferred to achieve control by inhibiting the reproduction capabilities of the insects. At concentrations above 60 mg per liter, for example, in the range of 600 mg per liter, the abscisic acid composition was lethal to the insect in this example.

TABLE I

| Food Plant and Treatment | Insect Rearing Environment | No. of Adult Pairs | No. of Fertile Pairs | Total Eggs Laid | Mean No. Eggs/ Per Female | Total Viable Eggs Laid | Mean No. Viable Eggs Per Female | Mean Longevity of Fertile Females (Days) | Eggs Laid/ Female Fecund Day | Viable Eggs/ Female Fecund Day |
|---|---|---|---|---|---|---|---|---|---|---|
| Greenhouse grass + Abscisic Acid (ABA) - 6 mg/l | 24–29.5 C ("Hot") | 30 | 13 | 138 | 10.6 | 19 | 1.5 | 41.7 | .254 | .035 |
| Greenhouse grass + ABA - 60 mg/l | "Hot" | 30 | 17 | 247 | 14.5 | 114 | 6.7 | 33.4 | .436 | .201 |
| Greenhouse grass (No Treatment) | "Hot" | 29 | 21 | 518 | 24.7 | 301 | 14.3 | 36.6 | .674 | .392 |

EXAMPLE II

The Effects of Abscisic Acid on Fecundity and Egg Viability of *Xanthippes corallipes* treated as adults.

Methods: Newly emerged adult *Xanthippes carallipes* grasshoppers were collected from Willow Creek, Mont., U.S.A. and brought to Bozeman, Mont. and placed one pair per cage in standard cages constructed of cellulose acetate cylinders (205 mm diameter and 280 mm high) placed on 9 inch diameter aluminum cake pans filled with sandy soil. The cages were covered with copper screen lids.

The grasshoppers were fed 10 ml of bran and approximately 40 leaves of Balboa rye grass (Lolium sp.) approximately 100 mm in length once every three days. The grass bundle was wrapped with urethane foam strips and placed upright in a plastic vial (25 mm diameter×45 mm high) and filled with treatment solutions or distilled water with 5 ml/l ethyl alcohol. The treatment solutions were made by dissolving the appropriate amount of abscisic acid in 5 ml of ethyl alcohol and diluting to one liter to make concentrations of 6 mg/l, 60 mg/l and 600 mg/l. The food vials were embedded into the sand at the bottom of the cages.

Cages were disassembled each morning and the sand sifted to obtain egg pods. Three ml of bran were placed on the soil in each cage after sifting.

Egg pods were placed upright in plastic pill vials and filled with the same sand mixture, watered and incubated at 25° C. for thirty days. Twice weekly egg pods were watered to maintain viability. At the end of thirty days, egg pods were peeled, eggs counted, and fixed in Bouin's solution. After fixation, eggs were rinsed in 70% alcohol, membranes peeled and viability determined. Fecundity and egg viability data include all eggs laid for each female over her lifespan.

The fecundity and egg viability data for Xanthippes fed abscisic acid during the adult stage only are presented in Table II where clear reductions in the numbers of viable eggs laid are demonstrated.

TABLE II

The Effects of Abscisic Acid on the Fecundity and Egg Viability of *Xanthippes corallipes* (Acrididae, Orthoptera) when fed to Adults.

|  | Control | ABA 6 mg/l | ABA 60 mg/l | ABA 600 mg/l |
| --- | --- | --- | --- | --- |
| Total Number of Females | 13 | 12 | 12 | 13 |
| Females Laying Egg Pods | 5 | 7 | 5 | 6 |
| Total Eggs Laid | 247.0 | 529.0 | 637.0 | 272.0 |
| Total Viable Eggs Laid | 129.0 | 28.0 | 112.0 | 54.0 |
| Mean # Eggs/Female | 49.4 | 75.6 | 127.4 | 45.3 |
| Mean # Viable Eggs/Female | 25.8 | 4.0 | 22.4 | 9.0 |

EXAMPLE III

Test of the Effect of Abscisic Acid on Fecundity and Egg Viability of *Xanthippes corallipes* treated in Nymphal and Adult Stages.

Method: *Xanthippes corallipes* grasshoppers were reared from fourth and fifth instar nymphs 5 pair per cage in cellulose acetate cylinders (250 mm diameter × 280 mm), placed on 9 inch diameter aluminum cake pans filled with sandy soil. The cages were covered with copper screen lids.

The grasshoppers were fed 10 ml of bran and approximately 40 leaves of Balboa rye grass 100 mm in length per cage once every three days. The rye grass stood wrapped with foam sponge strips in a 25 mm diameter × 45 mm plastic vial filled with distilled $H_2O$ and differing concentrations of abscisic acid (6 mg/l; 60 mg/l; 600 mg/l) dissolved in 5 ml/l of ethyl alcohol. The control water solution had 5 ml/l of ethyl alcohol mixed with it. The feeding and watering vials were embedded in the sand.

Upon adult emergence, the animals were placed one pair per cage in the same cellulose acetate cages placed on deep dish aluminum pans (230 mm diameter × 75 mm) filled with sandy soil. The adults were fed and watered exactly like the nymphs. Daily, the cages were disassembled, the sand was sifted in search of egg pods, the cages were reassembled, and approximately 3 ml of bran was placed on the soil in the cages. Sifting occurred from the seventh day of adult female life.

Egg pods found in sifting were placed top side up in plastic pill vials filled with the same sandy soil that was found in the cages and were incubated at 25° C. for thirty days. They were kept moist by watering with distilled $H_2O$ twice weekly. At the end of incubation, the pods were peeled, and the eggs were counted and recorded as either viable or non-viable.

Each cage was terminated upon the aging and death of its female member.

The data for fecundity and egg viability for this experiment are shown in Table III.

TABLE III

The Effects of Abscisic Acid on Fecundity and Egg Viability of *Xanthippes corallipes* (Acrididae, Orthoptera) when fed to Nymphs and Adults.

|  | Control | ABA 6 mg/l | ABA 60 mg/l | ABA 600 mg/l |
| --- | --- | --- | --- | --- |
| Total Number of Females | 23 | 28 | 18 | 20 |
| Number of Females Laying Egg Pods | 4 | 3 | 2 | 7 |
| Total Number of Eggs Laid | 226 | 92 | 151 | 430 |
| Number of Viable Eggs Laid | 1 | 22 | 0 | 34 |
| Number of Eggs Laid/Female | 56.6 | 30.7 | 75.5 | 61.4 |
| Number of Viable Eggs/Female | .25 | 7.3 | 0.0 | 4.9 |

EXAMPLE IV

The Effects of Abscisic Acid on Fecundity and Egg Viability of *Melanoplus sanguinipes* (Acrididae, Orthoptera).

Methods: *Melanoplus sanguinipes* were obtained as fifth instar nymphs from stock cultures maintained at the U.S.D.A. Rangeland Insects Laboratory in Bozeman, Mont., U.S.A. These were reared five pairs per cage in rectangular cube-like aluminum frame cages with 3 screen sides and one plexiglass side, the latter with a door to permit access. The bottom of the cages was made of screen and had a hole in which a nine-ounce plastic Solo brand cup filled with sand was placed for oviposition.

Grasshoppers were fed 10 ml of bran in a glass petri dish and approximtely 40 leaves of rye grass (Lolium sp.) 100 mm in length wrapped in urethane foam strips, the bundle placed upright in plastic vials, once every two days. The plastic food vials were embedded in the sand to hold the food upright. Grass was watered with distilled water and the proper amounts of abscisic acid dissolved in 5 ml ethyl alcohol to make concentrations of 6, 60 and 600 mg/l. Control grass was watered with distilled water in which 5 ml ethyl alcohol was added.

Six replicates of four treatments formed a total of twenty-four cages. Sand cups in the cages were sifted daily, egg pods collected and incubated at 25° C. for a minimum of one week, then peeled and fixed in Bouin's solution. After eggs were fixed, Bouin's was replaced with 70% ethanol, membranes were removed and eggs were assessed for viability.

Fecundity and egg viability for *Melanoplus sanguinipes* regimens are presented in Table IV. Effective control was obtained with treatments of abscisic acid at all three concentrations with the mean numbers of viable eggs per female reduced to 0.45, 0.75 and 0.2 at the 6, 60 and 600 mg/l doses, respectively. The overall fecundity and viability of these females was lowered more than one might expect for this species for unknown reasons, and the viability of eggs from the control was exceptionally low. Differences between the control and the experimentally treated groups are apparent nevertheless.

TABLE IV

The Effects of Abscisic Acid on the Fecundity and Egg Viability of *Melanoplus sanguinipes* (Acrididae, Orthoptera)

|  | Control | ABA 6 mg/l | ABA 60 mg/l | ABA 600 mg/l |
|---|---|---|---|---|
| Total Number of Females | 30.0 | 30.0 | 30.0 | 30.0 |
| Females Laying Egg Pods | 20.0 | 20.0 | 20.0 | 20.0 |
| Total Number Eggs Laid | 156.0 | 97.0 | 60.0 | 80.0 |
| Number of Viable Eggs | 26.0 | 9.0 | 15.0 | 4.0 |
| Mean # of Eggs/Female | 7.8 | 4.85 | 3.0 | 4.0 |
| Mean # Viable Eggs/Female | 1.3 | .45 | .75 | .2 |

EXAMPLE V

This Example is to ascertain the effectiveness of the plant hormone, abscisic acid, in regulating the reproduction of the aphid *Rhopalosiphum padi* (Linn.) (Kaltenbach).

Materials and Methods:

Four regimens of ten cages each were established; ten cages were designated as the controls; ten cages each were treated with 6 mg/l, 60 mg/l and 600 mg/l of abscisic acid dissolved in 10 ml of ethanol and then diluted with distilled water. Cages were constructed of cellulose acetate cylinders (as described in the patent experiment) placed on end over sand filled 9" cake pans and covered at the top with organdy cloth. Aphids were fed barley plants collected weekly from a field site and stored at 12° C. between collections. Leaves were clipped from the barley and wrapped with a strip of urethane sponge around their bases and placed upright in a plastic pill vial. These food vials were placed upright in the sand at the bottom of each cage. Abscisic acid was misted with a spray bottle on the leaves and aphids, the sponges in the food vials were soaked and the vial filled with the appropriate concentrations of abscisic acid solutions. Wilted or dried leaves were removed and replaced with fresh leaves daily.

Two apterous parents (P$_1$) were placed in each cage and one was allowed to reproduce five offspring (F$_1$). The P$_1$ aphids were then removed from the cage. The F$_1$ generation was reared to the 4th instar and one aphid was chosen to be the parent of the F$_2$ and the others were removed. When five F$_2$ nymphs were produced and raised to the 4th instar, all but one aphid were removed. This parent was allowed to give birth to 5 F$_3$ nymphs and these were reared to the 4th instar. All but one was again removed from the cage. This F$_3$ parent then was reared for three days after the birth of the first offspring and all progeny then were counted. This procedure was necessary to eliminate possible maternal effects on fecundity which might result from crowding, and to insure that the treatment effect was being measured rather than some other prior environmental effect which might be transmitted from mother to offspring.

Aphids which died or were lost prior to the birth of the F$_3$ generation, were replaced with an aphid of a comparable generation from the same treatment regimen. Deaths occurring in the F$_3$ generation were assumed to result from the treatments.

Results: Results are summarized in the following Table V as follows: The mean fecundity of females in the control group was 34.10; those treated with 6 mg/l ABA had a mean of 22.10; with 60 mg/l ABA 15.8 and those with 600 mg/l had a mean of 8 offspring per female. These means were compared with analysis of variance and found to be significantly different (P=0.0000). When the number of offspring produced per reproductive day were compared again, the treatment groups differed from the controls. The controls produced 11.37 offspring per day; aphids treated with 6 mg/l ABA had 7.617 offspring per day, those with 60 mg/l ABA had 5.733 and finally, those treated with 600 mg/l had 2.749 offspring per day. These means are again highly significantly different when compared by analysis of variance (P=0.0000). $X^2$ analysis of the proportion of females which died before the third day of reproduction also yielded significant differences between treatment and the control (P=0.035), indicating that the treatment was lethal to some females. Tests for significant deviation from a straight line of treatments with respect to deaths were not significant, indicating a linear dose-response relationship exists.

A significant reduction in the numbers of offspring resulted from treatment of maternal aphids with water solutions of abscisic acid applied to them and their host plant (barley) by watering and misting. A linear dose-response curve was obtained for both total fecundity and the number of offspring per reproductive day, and for the incidence of deaths in the respective treatment regimens.

TABLE V

Fecundity and Longevity of F$_3$ Aphids fed Barley Treated with Abscisic Acid

|  | Days of Reproduction of each female | Offspring of each Female | Mean Offspring | Mean # Offspring/Reproductive Day |
|---|---|---|---|---|
| Control | 3,3,3,3,3,3,3,3,3,3, | 32,24,53,44,43,13,39,29,33,31 | 34.10 | 11.370 |
| ABA 6 mg/l | 3,0,3,3,3,2,3,3,3,3 | 15,0,22,23,23,15,42,18,20,42 | 22.10 | 7.617 |
| ABA 60 mg/l | 3,3,0,3,3,0,1,1,3,3 | 29,26,0,31,22,0,3,4,25,18 | 15.80 | 5.733 |
| ABA 600 mg/l | 0,3,3,2,3,3,3,0,3,3 | 0,9,21,5,15,10,0,0,13,7 | 8.00 | 2.749 |

EXAMPLE VI

The Effects of Abscisic Acid on the Fecundity and Egg Viability of *Oncopeltus fasciatus*.

Methods: Four regimens were established to test the effects of abscisic acid on the fecundity and egg viability of *Oncopeltus fasciatus*, the milkweed bug (Order Hemiptera, Insecta). In each regimen, thirteen females and ten males were tested. Treatments were started beginning with the fifth instar nymphs since at that stage the sexes can be easily recognized externally. Abscisic acid was added to distilled water provided for drinking at concentrations of 6 mg/liter, 60 mg/l and 600 mg/l. Untreated distilled water was given to the control regimen. A diet of sunflower seeds soaked in the same concentrations of abscisic acid or distilled water was provided. At such feeding, eight seeds were soaked in 1 ml of treatment solution for 15 minutes and the excess solution was drained away. Water and food were replaced and the cages cleaned twice weekly.

Petri dishes 10 mm in diameter were filled with cotton to provide oviposition sites. Eggs were collected daily, counted and recorded, placed on moistened filter paper in a plastic petri dish and incubated at 25° C. The number of hatched eggs was counted and recorded daily. The sex of dead insects was noted and recorded daily and a daily count made of the living adult males and females in each regimen. Regimens were terminated when all females had died.

Egg laying rates were calculated for each regimen by dividing the total number of eggs laid during the experiment by the sum of the adult female reproductive days. The sum of adult female reproductive days was calculated by totalling the number of days all adult females lived during their entire egg laying period.

Females fed abscisic acid at 60 mg/l laid the fewest eggs, and the number of viable eggs was only 56% that of the control. The group fed ABA at 600 mg/l, however, had viability 10% lower than the control, although their fecundity was not significantly different. No data are yet available concerning the effects of feeding more than one generation. The reduction in numbers with abscisic acid was not as dramatic as that observed when the treatment is made on leaf-eating insects. The data is given in Table VI.

TABLE VI

Fecundity and Egg Viability Data for *Oncopeltus fasciatus* Fed Abscisic Acid after the Fifth Nymphal Stage

| Treatment | Control | ABA 6 mg/l | ABA 60 mg/l | ABA 600 mg/l |
|---|---|---|---|---|
| Number of Females | 13 | 13 | 13 | 13 |
| Total Eggs Laid | 2986.0 | 2586.0 | 1173.0 | 2923.0 |
| Total Viable Eggs | 2400.0 | 2094.0 | 1347.0 | 1992.0 |
| Total Eggs Laid/Female | 229.7 | 198.9 | 136.4 | 224.9 |
| Total Viable Eggs/Female | 184.6 | 161.1 | 103.7 | 153.2 |
| Number of Female Reproductive Days (Female only) | 173.0 | 131.0 | 97.0 | 142.0 |
| Eggs/Female Day | 17.1 | 19.7 | 18.3 | 20.6 |
| Viable Eggs/Female Day | 13.7 | 16.0 | 13.9 | 14.0 |
| Comparison of Viable Eggs in the Treatment vs. Control (%) | | 87.3% | 56.1% | 83.0% |
| Percentage of Viable/Non-Viable Eggs Within a Treatment Group | 80.4% | 81.0% | 76.0% | 70.6% |

EXAMPLE VII

The Effects of Abscisic Acid on the Fecundity and Egg Viability and Larval Development of *Musca domestica* (Diptera, Insecta).

The common housefly was reared from eggs taken from stock cultures of *Musca domestica* obtained from the U.S.D.A. Metabolism and Radiation Laboratory in Fargo, No. Dakota, United States. The methods reported here are those used in that laboratory for mass rearing of *M. domestica*.

Methods: Two to four hundred larvae were reared in one-gallon glass jars on a diet consisting of the following ingredients:
1120 ml baker's yeast solution (147 gms yeast mixed with 7840 ml distilled water)
2000 ml Ralston Purina Animal Diet (CSMA)

Abscisic acid dissolved in 10 ml of ethyl alcohol was added to the yeast solution to make concentrations 6 mg/l, 60 mg/l and 600 mg/l. The control diet had 10 ml of ethyl alcohol added to the solution.

Two replicates of each of the four regimens were prepared. Larvae were reared in the jars until all had undergone pupation. These pupae were removed from the jars and counted. Those flies which emerged from pupal cases were separated into cages. Data for the numbers and percentages of pupae which failed to emerge are presented in Table VIIA.

The adult flies from different larval rearing regimens were maintained in cages constructed of plastic cylinders (205 mm diameter × 280 mm height) taped to 9 inch diameter aluminum cake pans. Round openings were cut into the sides of the cylinders and cloth sleeves attached to permit access. Cages were covered with a fine nylon mesh cloth held to the top of the cylinder by rubber bands. Adult flies were fed a mixture of powdered milk-sugar-powdered egg (19.5:7:2 volume ratio). This food mixture was fed in plastic petri dishes (35 mm diameter × 10 mm height) and changed weekly. Drinking water was provided using a plastic vial covered by a plastic lid through which a hole had been cut to permit a 40 mm long cotton roll wick to be inserted. The flies were watered twice weekly with distilled water containing abscisic acid dissolved in 5 ml of ethyl alcohol in the amounts to make concentrations of 6 mg/l, 60 mg/l and 600 mg/l. The control was given distilled water with 5 ml/l of ethyl alcohol added to it.

An oviposition mixture was prepared weekly consisting of the following:
1500 ml distilled water
300 ml by volume powdered milk
2 gms baker's yeast
12.5 gms ammonium carbonate.

Approximately 10 ml of the mixture was saturated into cotton placed in a clear plastic 9 ounce Solo brand cup and the cotton partially covered by wrinkled cotton muslin cloth to provide protection to the egg-laying flies. These egg laying sites were placed in each cage for 24 hours and replaced daily. The eggs found in these cups were counted daily and data recorded. 100 eggs as they were available were incubated at 25° C. for 24 hours. At the end of the incubation, the unhatched eggs in each sample were counted and recorded to provide egg viability data for each of the treatment regimens.

The experiment was terminated when all of the flies in the cage had died (30-40 days from adult emergence).

The fecundity and egg viability data for different treatment regimens and control are presented in Table VIIB.

The initial regulating effect of abscisic acid was observed in the reduced percentages of flies emerging from the pupal cases. At the 6 mg/l dose, an average of 75% of the flies failed to emerge compared with a control average in which 26% failed to hatch.

Of those flies which did emerge and went on to lay eggs, the group fed 6 mg/l abscisic acid produced an estimated average number of viable eggs per female one/third that of the control (abscisic acid 6 mg/l=209.49, control—322.35). The group fed ABA at 600 mg/l had an estimated 303.82 viable eggs per female while the group fed ABA at 60 mg/l laid an estimated 502.21 viable eggs per female.

The effects of the ABA 6 mg/l dose then are apparent first in failure of fed larvae to emerge from the pupae as adults, those which do emerge lay many fewer eggs per female and those are one-third less viable than the controls.

The overall effect of feeding abscisic acid at 6 mg/l to a population of house flies should be very low numbers reproduced and those with low potential for laying viable offspring. We have not yet tested to determine whether there are cumulative effects over time, that is, after two or three generations whether the effects become more apparent.

The Effects of Abscisic Acid on the Pupal to Adult Emergence, Fecundity and Egg Viability of *Musca domestica* (Diptera, Insecta).

TABLE VIIA

Number and Percentage of Hatch from Pupae Following Larval Feeding with Abscisic Acid

| Treatment | Cage | Pupae Collected | Pupae Emerged | Percent Emergence | |
|---|---|---|---|---|---|
| Control | 1 | 355 | 267 | 75.21 | |
| Control | 2 | 369 | 268 | 72.63 | |
| Control totals | | 724 | 535 | Control average | 73.90% |
| ABA-6 | 1 | 219 | 38 | 17.35 | |
| ABA-6 | 2 | 204 | 70 | 34.31 | |
| ABA-6 totals | | 423 | 108 | ABA-6 average | 25.53% |
| ABA-60 | 1 | 269 | 38 | 59.48 | |
| ABA-60 | 2 | 258 | 70 | 49.22 | |
| ABA-60 totals | | 527 | 108 | ABA-60 average | 54.46% |
| ABA-600 | 1 | 335 | 160 | 22.09 | |
| ABA-600 | 2 | 522 | 127 | 69.35 | |
| ABA-600 totals | | 857 | 287 | ABA-600 average | 50.88% |

The Effects of Abscisic Acid on the Pupal to Adult Emergence, Fecundity and Egg Viability of *Musca domestica* (Diptera, Insecta).

TABLE VIIB

Fecundity and Egg Viability Data for Regimens of *Musca domestica* fed Abscisic Acid During the Larval Stages

| Treatment | Cage | Total Egg Count | Number of Females | Eggs per Female | Total Egg Sample Size | Total Hatched from Egg Samples | Percentage of Eggs Hatched | Estimated Number of Viable Eggs/Female |
|---|---|---|---|---|---|---|---|---|
| Control | 1 | 4299 | 9 | 477.7 | 1313 | 1168 | 88.96 | |
| Control | 2 | 3029 | 10 | 302.9 | 941 | 716 | 79.09 | |
| Control totals | | 7328 | 19 | 385.68 | 2254 | 1884 | 83.58 | 322.35 |
| ABA-6 | 1 | 3992 | 10 | 399.2 | 1611 | 1117 | 69.34 | |
| ABA-6 | 2 | 1877 | 10 | 187.7 | 896 | 740 | 82.59 | |
| ABA-6 | 3 | 2180 | 10 | 218.0 | 960 | 850 | 88.54 | |
| ABA-6 totals | | 8049 | 30 | 268.3 | 3467 | 2707 | 78.08 | 209.49 |
| ABA-60 | 1 | 4926 | 10 | 492.6 | 1054 | 944 | 89.56 | |
| ABA-60 | 2 | 5159 | 10 | 515.9 | 1385 | 1106 | 79.86 | |
| ABA-60 | 3 | 7530 | 10 | 753.0 | 1563 | 1373 | 87.84 | |
| ABA-60 totals | | 17615 | 30 | 587.17 | 4002 | 3423 | 85.53 | 502.21 |
| ABA-600 | 1 | 4608 | 10 | 460.8 | 961 | 681 | 70.86 | |
| ABA-600 | 2 | 4935 | 10 | 493.5 | 1395 | 689 | 49.39 | |
| ABA-600 | 3 | 5003 | 10 | 500.3 | 1021 | 746 | 73.07 | |
| ABA-600 totals | | 14546 | 30 | 484.87 | 3377 | 2116 | 62.66 | 303.82 |

EXAMPLE VIII

Test of the Effect of Abscisic Acid Placed on the Eggs of *Drosophila melanogaster*.

Method: Fruit flies were reared in half-pint milk jars on an artificial diet consisting of the following:
775 ml/l distilled $H_2O$,
100 ml/l Potassium Phosphate Dibasic buffer (9.47 gms/l),
125 ml/l Potassium Phosphate Monobasic buffer (9.08 gms/l),
100 gms/l yeast,
100 gms/l sugar,
50 gms/l cornmeal
7.5 gms/l agar,
15 ml/l Propionic Acid.
An egg laying medium was prepared consisting of the following:
850 ml/l distilled $H_2O$,
7.5 gms/l agar,
100 gms/l yeast,
5 ml/l Ethyl Alcohol,
135 ml/l Welch's Grape Juice.

Approximately 5 ml of the medium was placed in 40 mm diameter×5 mm plastic petri dishes. A piece of fine meshed nylon cloth was cut to fit over the medium in each dish and the fruit flies were given an egg laying opportunity (approximately 2 hours) by placing the dish on the top of the jar, and inverting the jar. At the end of this opportunity, the jars were reinverted, the dishes were taken off, and the eggs (laid on the nylon cloth) were removed from the medium.

Proper amounts of abscisic acid were dissolved in 5 ml of ethyl alcohol and diluted with $H_2O$ to 6 mg/l, 60 mg/l and 600 mg/l concentrations. The control solution was 5 ml/l to ethyl alcohol in distilled water. About 2 ml of each solution was saturated in filter paper placed in the bottoms of four 90 mm diameter×20 mm plastic petri dishes. Fifty eggs each were placed on the saturated filter paper and eggs incubated at 25° C. for 48 hours. After incubation, the number of unhatched eggs were counted and recorded.

The tests were first run using two different generations of Drosophila over two separated three-day periods.

Abscisic Acid as a Direct Ovicide in *Drosophila melanogaster*

Test of the effects of Abscisic Acid Placed Topically on the Eggs of Fruit Flies. Active compound Dissolved in 5 ml of Ethyl Alcohol, and Added to Water.

TABLE VIIIA

| | (First Run) | | | |
|---|---|---|---|---|
| Treatment | Control | ABA-6/1 | ABA-60/1 | ABA-600/1 |
| Hatched | 42 | 16 | 30 | 26 |
| Unhatched | 8 | 34 | 20 | 24 |
| Total Treated | 50 | 50 | 50 | 50 |

TABLE VIIIB

| | (Second Run) | | | |
|---|---|---|---|---|
| Treatment | Control | ABA-6/1 | ABA-60/1 | ABA-600/1 |
| Hatched | 31 | 18 | 16 | 29 |
| Unhatched | 19 | 32 | 34 | 21 |
| Total Treated | 50 | 50 | 50 | 50 |

Industrial Applicability

The abscisic acid insect control compositions and methods of this invention, which reduce the ability of the insects to reproduce, are useful in providing an environmentally safe procedure for controlling the proliferation and undesired destruction by insect pests.

The invention has been described herein with reference to certain preferred embodiments. However, as obvious variations thereon will become apparent to those skilled in the art, the invention is not considered to be limited thereto.

I claim:

1. A method for the control of houseflies characterized by the steps of applying a reproduction-inhibiting amount of abscisic acid in a concentration of about 6 mg per liter of an aqueous carrier, to food on which said houseflies feed, thereby reducing the ability of the houseflies to reproduce and thus control proliferation of the houseflies.

2. A method for the control of fruit flies, characterized by the step of applying a reproduction-inhibiting amount of abscisic acid contained in an aqueous carrier in a concentration ranging from at least about 6 mg per liter to about 600 mg per liter directly to eggs of the fruit fly, thereby reducing the ability of the fruit fly to reproduce and thus control proliferation of the fruit flies.

* * * * *